United States Patent [19]

Jones

[11] 4,303,649

[45] Dec. 1, 1981

[54] 1-PHENYL-2-AMINOETHANOL DERIVATIVES

[75] Inventor: Geraint Jones, Prestbury, England

[73] Assignee: Imperial Chemical Industries Limited, London, England

[21] Appl. No.: 43,425

[22] Filed: May 29, 1979

[30] Foreign Application Priority Data

Jun. 15, 1978 [GB] United Kingdom ............... 27026/78

[51] Int. Cl.³ .......................................... C07C 103/82
[52] U.S. Cl. ................................ 424/177; 260/404.5; 560/138; 424/311; 424/324; 424/312
[58] Field of Search ............ 260/558 A, 559 A, 404.5, 260/112.5; 560/138; 424/311, 312, 177, 324

[56] References Cited

U.S. PATENT DOCUMENTS

| | | | |
|---|---|---|---|
| 3,944,611 | 3/1976 | Smith | 260/562 R |
| 4,038,417 | 7/1977 | Nelson | 424/330 |
| 4,041,075 | 8/1977 | Smith | 260/558 P |

FOREIGN PATENT DOCUMENTS 2745222  4/1978  Fed. Rep. of Germany ...... 560/138

*Primary Examiner*—Robert Gerstl

*Attorney, Agent, or Firm*—Cushman, Darby & Cushman

[57] ABSTRACT

The invention concerns new topical anti-inflammatory 1-phenyl-2-aminoethanol derivatives of the general formula:

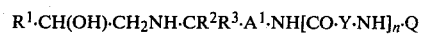

$R^1 \cdot CH(OH) \cdot CH_2NH \cdot CR^2R^3 \cdot A^1 \cdot NH[CO \cdot Y \cdot NH]_n \cdot Q$ wherein $R^1$ is a phenyl bearing specific combinations of (2–12C)alkanoyloxy,[(2–12C)alkanoyloxy]methyl,-chloro and amino substituents, $R^2$ and $R^3$ are independently hydrogen or (1–4C)alkyl, $A^1$ is a (1–4C)alkylene, Y is a (1–4C)alkylene optionally bearing a (1–4C)alkyl or benzyl, n is an integer from 1 to 4, and Q is an optionally substituted benzoyl, phenylacetyl, or phenoxyacetyl together with the acid-addition salts thereof; and the pharmaceutical compositions thereof, for use in the treatment of inflammatory skin diseases and conditions. The invention also concerns processes for the manufacture of derivatives of formula I.

A representative compound of the invention is 1-[3,4-bis(pivaloyloxy)phenyl]-2-{2-[(N-benzoylglycyl)amino]-1,1-dimethyl-ethylamino}ethanol.

9 Claims, No Drawings

1-PHENYL-2-AMINOETHANOL DERIVATIVES

This invention concerns novel 1-phenyl-2-aminoethanol derivatives which possess anti-inflammatory properties when applied topically to an area of inflammation, and in addition it concerns pharmaceutically compositions of, methods of manufacture of, and methods of treatment using, such derivatives.

It is known from our earlier work that certain 1-phenoxy-3-{[(acrylamino)alkanoylamino]alkylamino}-propan-2-ol derivatives possess β-adrenergic blocking properties (West German Offenlegungsschrift No. 2,745,222). We have now discovered, and herein lies our invention, that certain new 1-phenyl-2-aminoethanol derivatives bearing an [(acrylamino)alkanoylamino]alkyl substituent on the amino radical surprisingly possess topical anti-inflammatory properties, that is they possess anti-inflammatory properties when applied topically to an area of inflammation.

Accordingly the invention provides a 1-phenyl-2-aminoethanol derivative of the formula:

$R^1.CH(OH).CH_2NH.CR^2R^3.A^1.NH[CO.Y.NH]_n.Q$    I wherein $R^1$ is a radical of the formula:

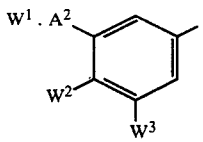

II in which $W^1$ is a (2–12 C)alkanoyloxy radical, one of $W^2$ and $W^3$ is hydrogen and the other of $W^2$ and $W^3$ is a (2–12 C)-alkanoyloxy radical, and $A^2$ is a direct bond or a methylene diradical; or $R^1$ is a phenyl, 2-chlorophenyl or 3,5-dichloro-4-aminophenyl radical; $R^2$ and $R^3$ are independently hydrogen or (1–4 C)alkyl radicals; $A^1$ is a (1–4 C)alkylene diradical; Y is a (1–4 C)alkylene diradical optionally bearing a (1–4 C)alkyl or benzyl substituent; n is an integer from 1 to 4; and Q is benzoyl, phenylacetyl or phenoxyacetyl radical optionally bearing a nuclear substituent selected from halogeno, (1–4 C)alkyl, (1–4 C)-alkoxy and trifluoromethyl radicals; provided that when n is other than 1, Y in the individual diradicals of the formula [CO.Y.NH] may have the same or different values; or a pharmaceutically acceptable acid-addition salt thereof.

It will be observed that a compound of formula I possesses at least one asymmetric carbon atom, that is the carbon atom bearing $R^1$, and depending on the nature of its substituents, also additional asymmetric carbon atoms, and can therefore exist in racemic and optically-active forms. This invention relates to the racemic form of a compound of formula I or to any optically-active form which possesses anti-inflammatory activity, it being well known in the art how to prepare optically active forms by resolution of the racemic form, or by synthesis from optically active starting materials, and how to determine the topical anti-inflammatory activity by the standard tests described hereinbelow.

A particular value for $W^1$, and for $W^2$ or $W^3$ when they are (2–12 C)alkanoyloxy radicals, is, for example, a 2,2-dimethylpropionyloxy (pivaloyloxy), isobutyryloxy, n-pentanoyloxy (valeryloxy), or 3,3-dimethylbutyryloxy radical.

A particular value for $R^2$ or $R^3$ when it is a (1–4 C)alkyl radical is, for example, a methyl radical.

A preferred value for $R^2$ and $R^3$ is, for example, when they are both hydrogen or methyl radicals, of which the latter value is especially preferred.

A particular value for $A^1$ is, for example, a methylene or ethylene diradical, of which a methylene diradical is preferred.

A particular value for Y is, for example, a methylene, ethylene, or trimethylene diradical, and a particular value for an optional (1–4 C)alkyl substituent is, for example, a methyl or ethyl radical.

A particular value for the diradical of the formula [CO.Y.NH] is, for example, a glycyl ($CO.CH_2NH$), alanyl [$CO.CH(CH_3).NH$], β-alanyl ($CO.CH_2CH_2NH_2$) or phenylalanyl [$CO.CH(CH_2Ph).NH$] diradical, of which values a glycyl diradical is particularly preferred.

A preferred value for n is the integer 1 or 2.

When n is 2, a particular value for the diradical of the formula $[CO.Y.NH]_n$ as previously defined, is, for example, a glycylglycyl ($CO.CH_2NH.CO.CH_2NH$), glycylalanyl [$CO.CH_2NH.CO.CH(CH_3).NH$] or alanylglycyl [$CO.CH(CH_3).NH.CO.CH_2NH$] diradical, of which values a glycylgylcyl diradical is particularly preferred.

A particular value for a nuclear substituent, which may be present when Q is an optionally substituted benzoyl, phenylacetyl or phenoxyacetyl radical, is, for example, a fluoro, chloro, bromo, methyl, methoxy or trifluoromethyl radical.

A preferred value for $R^1$ is when it is a 3,4-bis[(2–12 C)alkanoyloxy]phenyl radical [such as a 3,4-bis(-pivaloyloxy)phenyl radical], a 3,5-bis[2–12 C)-alkanoyloxy]phenyl radical [such as a 3,5-bis(-pivaloyloxy)-phenyl radical], a 3-[(2–12 C)alkanoyloxymethyl]-4-[(2–12 C)alkanoyloxy]phenyl radical (such as a 3-valeryloxymethyl-4-valeryloxyphenyl radical), or a 3,5-dichloro-4-aminophenyl radical; and particular groups of compounds of the invention are comprised by those compounds of formula I wherein $R^1$ has one of the above preferred values, and in each group $R^2$, $R^3$, $A^1$, Y, n and Q have any of the previously defined values; together with the pharmaceutically acceptable acid-addition salts thereof.

A preferred group of compounds of the invention comprises those compounds of formula I wherein $R^1$ has any one or more of the above preferred values, $R^2$ and $R^3$ are methyl radicals, $A^1$ is a methylene diradical, the diradical of the formula $[CO.Y.NH]_n$ is a glycyl, alanyl, phenylalanyl or glycylglycyl diradical, and Q is a benzoyl, phenylacetyl or phenoxyacetyl radical; together with the pharmaceutically acceptable acid-addition salts thereof.

A yet further preferred group of compounds of the invention comprises those compounds of formula I wherein the diradical of the formula $[CO.Y.NH]_n$ is a glycyl or glycylglycyl diradical, and $R^1$, $R^2$, $R^3$, $A^1$ and Q have any of the above defined values; together with the pharmaceutically acceptable acid-addition salts thereof.

A particular acid-addition salt of a compound of formula I is, for example, a salt derived from an acid having a pharmaceutically acceptable anion, for example from an inorganic acid, for example hydrochloric, hydrobromic, phosphoric or sulphuric acid, or from an organic acid, for example oxalic, tartaric, lactic, fumaric, citric, acetic, salicylic, benzoic, β-naphthoic, methane sulphonic or adipic acid. These salts may contain one or two molecular equivalents of acid.

Specific compounds of formula I are described in the accompanying Examples. However, of these, 1-[3,4-bis(pivaloyloxy)phenyl]-2-{2-[(N-benzoyl-glycyl)amino]1,1-dimethyl-ethylamino}ethanol, 1-[3,4-bis(pivaloyloxy)-phenyl]-2-{2-[(N-phenylacetyl-glycyl)amino]-1,1-dimethylethylamino}ethanol, 1-[3,4-bis(pivaloyloxy)phenyl]-2-{2-[(N-phenylacetyl-glycyl)glycyl-amino]-1,1-dimethyl-ethylamino}ethanol, 1-(3,5-dichloro-4-aminophenyl)-2-{2-[(N-phenoxyacetyl-glycyl)amino]-1,1-dimethyl- ethylamino}ethanol and 1-(3,5-dichloro-4-aminophenyl)-2-{2-[(N-phenylacetyl-glycyl)glycyl-amino[-1,1-dimethyl-ethylamino}ethanol, or a pharmaceutically acceptable acid-addition salt thereof, are of special interest.

The compounds of formula I may be manufactured by any chemical process known to be useful for the manufacture of chemically analogous compounds, for example those processes described in West German Offenlegungsschrift No. 2,745,222. Such processes are provided as a further feature of the invention and are illustrated by the following preferred processes wherein $R^1$, $R^2$, $R^3$, $A^1$, Y, n and Q have the meanings previously defined.

(a) A glyoxal of the formula:

$$R^1CO.CHO \qquad \qquad III$$

is reacted with an amino compound of the formula:

$$H_2N.CR^2R^3.A^1. NH[CO.Y.NH]_n.Q \qquad IV$$

under reducing conditions.

Particular suitable reducing conditions are provided by using, for example, an alkali metal cyanoborohydride, for example sodium cyanoborohydride, conveniently in an inert solvent or diluent, for example acetonitrile, methanol, ethanol or 2-propanol and at a temperature in the range, for example −20° C. to 30° C. When sodium cyanoborohydride is used, the reaction is preferably carried out at or near pH 4, for example in the presence of acetic acid. Other standard reducing conditions may be suitable provided they are compatible with the substituents present in the starting material.

It will be appreciated that processes of the above general type are known as reductive alkylations, and proceed at least in part through an intermediate of the formula:

$$R^1.U.CH=N.CR^2R^3.A^1.NH[CO.Y.NH]_n.Q \qquad V$$

wherein U is a hydroxymethylene diradical and/or of the formula V wherein U is a carbonyl diradical. Such an intermediate of formula V wherein U is a hydroxymethylene or a carbonyl diradical (or a mixture thereof) may be prepared and reduced in two separate stages in process (a) if desired.

The starting materials of formula III may be obtained, for example, by selenium dioxide oxidation of an acetophenone of the formula:

$$R^1CO.CH_3 \qquad \qquad VI$$

in an appropriate solvent, for example aqueous dioxan, at a temperature in the range, for example, 50°–150° C., optionally followed by hydrate, acetal or hemi-acetal formation, in which form they may also be employed in the above process (a).

Alternatively, the starting materials of formula III may be conveniently obtained by dimethyl sulphoxide oxidation of the appropriate phenacyl bromide derived by bromination of the corresponding acetophenone of formula VI, for example as illustrated in the Examples hereinafter.

The amino compounds of formula IV may be obtained for example, by reaction of the appropriate acid of the formula:

$$HO.[CO.Y.NH]_n.Q \qquad VII$$

with a diamine of the formula:

$$H_2N.CR^2R^3.A^1.NH_2 \qquad VIII$$

The acid of formula VII is preferably first converted to a reactive derivative such as its mixed anhydride with a (1–4 C) acid carbonate, obtainable by reacting the acid of formula VII with a [(1–4 C)alkoxy]carbonyl chloride in the presence of a tertiary base such as N-methylmorpholine. This procedure is illustrated in the accompanying Examples and enables the amino compounds of formula IV to be prepared at a temperature at or below room temperature, thus resulting in the minimum of racemisation when the diradical of formula [CO.Y.NH]$_n$ contains an optically active α-amino acyl diradical.

The acids of formula VII are themselves obtained by acylation of the appropriate amino acid of the formula:

$$HO.[CO.Y.NH]_n.H \qquad IX$$

with an acylating agent derived structurally from an acid of the formula Q.OH, for example a chloride or bromide of such an acid, using conventional reaction conditions, for example as illustrated in the accompanying Examples.

(b) A compound of the formula:

$$R^1.CO.CH_2NH.CR^2R^3.A^1.NH[CO.Y.NH]_n.Q \qquad X$$

is reduced.

The reduction may be carried out using any agent generally known for reducing aromatic ketones, but which is compatible with the other substituents present in the starting material of formula X. Thus the reduction may be carried out by means of an alkali metal borohydride, for example sodium borohydride or cyanoborohydride, in an appropriate diluent or solvent, for example methanol, ethanol or 2-propanol, or by means of catalytic hydrogenation (which is preferred), for example with hydrogen in the presence of a palladium, platinum or nickel catalyst and preferably under a pressure of hydrogen of, for example, up to 5 bar in a diluent or solvent, for example ethanol or acetic acid, and in either case, at a temperature of, for example −20° C. to 50° C., and conveniently at or near normal room temperature, for example at 15° to 30° C.

The starting materials of formula X may be obtained by reacting a phenacylhalide of the formula:

$$R^1.CO.CH_2.Hal \qquad XI$$

wherein Hal. is a chloro or bromo radical, with an amino compound of the formula IV.

This reaction is conveniently carried out at or near normal room temperature, for example from 15° to 30° C., and in a diluent or solvent, for example ethanol, dioxan, chloroform or acetonitrile. It may also be carried out in the presence of an acid-binding agent, for example pyridine, triethylamine or an alkali metal carbonate or bicarbonate, or an excess of the amino compound of formula IV.

A compound of formula I in free base form may be converted into a pharmaceutically acceptable acidaddition salt by reaction with a suitable acid as defined hereinbefore and by conventional means which avoid hydrolysis of any ester groups. Alternatively, when a hydrogen chloride or bromide salt is required, this may be conveniently obtained by producing a stoichiometric amount of the hydrogen halide in situ by catalytic hydrogenation of the appropriate benzyl halide, preferably in an inert solvent or diluent, for example ethanol, and at, or near, room temperature.

The compounds of formula I may conveniently be used as their pharmaceutically acceptable acidaddition salts.

Optically-active form of a compound of formula I may be obtained, for example, by conventional resolution of the corresponding racemic form of a compound of formula I. Thus a racemic form of a compound of formula I may be reacted with an optically-active acid, followed by fractional crystallisation of the diastereoisomeric mixture of salts thus obtained from a diluent or solvent, for example ethanol, whereafter the optically-active form of a compound of formula I may be liberated by treatment under conditions which avoid loss of sensitive groups when present, for example by using anion exchange chromatography. A particularly suitable optically-active acid is, for example (+)- or (−)-O,O-di-p-toluoyltartaric acid, or (−)-2,3:4,5-di-O-isopropylidene-2-keto-L-gulonic acid.

In addition, compounds, of formula I having at least some of their asymmetrically substituted carbon atoms with a specific optical configuration may also be obtained by incorporating optically active starting materials, such as optically active α-amino acids, in the above synthetic processes.

As stated above, the compounds of formula I possess anti-inflammatory activity when applied topically to an area of inflammation and, in particular, are therefore useful in treating inflammatory diseases or inflammatory conditions of the skin, in warm-blooded animals.

The anti-inflammatory properties of a compound of formula I may be demonstrated in a standard test involving the inhibition of croton oil induced inflammation on the mouse ear. The activity of an individual compound of formula I in this test depends upon its particular chemical structure, but in general compounds of formula I produce a significant inhibition of the inflammation at a topically applied dose of 0.30 mg. per ear or much less.

Another standard test in which the antiinflammatory properties of a compound of formula I may be demonstrated involves the inhibition of oxazolone induced contact sensitivity on the mouse ear. In general, compounds of formula I produce significant inhibition of the inflammation in this test at a topically applied dose of 0.6 mg. per ear, or less.

No overt toxic effects are detected at the active doses in either of the above tests, with the compounds of formula I described herein.

In general, a compound of formula I may be used in the treatment of inflammatory diseases or inflammatory conditions of the skin in an analogous manner to that in which known topically active antiinflammatory agents, for example the topically active steroids, are used.

When used for the topical treatment of an area of inflammation affecting the skin of a warmblooded animal, for example man, a compound of formula I may be administered topically at a dose in the range 100 μg. to 15 mg./cm.$^2$, or at an equivalent dose of a pharmaceutically acceptable acid-addition salt thereof, and, if necessary, a dose in this range is repeated at intervals of, for example, 4–12 hours. It will be appreciated that the total daily amount of a compound of formula I administered depends on the extent and severity of the inflammation under treatment.

By way of example only, when 1[3,4-bis-(pivaloyloxy)phenyl]-2-{2-[(N-benzoyl-glycyl)amino]-1,1-dimethylethylamino}ethanol is used for the topical treatment of an area of inflammation affecting the skin of a warmblooded animal, for example man, a dose in the range 10 μg. to 5 mg./cm$^2$., or an equivalent amount of a pharmaceutically acceptable acid-addition salt thereof, is administered topically, and if necessary is repeated at intervals of 4–12 hours.

The compounds of formula I may be administered in the form of pharmaceutical compositions and according to a further feature of the invention there is provided a pharmaceutical composition comprising a compound of formula I, or a pharmaceutically acceptable acid-addition salt thereof, in association with a pharmaceutically acceptable diluent or carrier, in a form suitable for topically administration, for example in the form of an ointment, gel, aqueous or oily solution or suspension, emulsion or aerosol formulation. A pharmaceutical composition according to this aspect of the invention may contain from 0.1% to 10% w/w of a compound of formula I or an equivalent amount of a pharmaceutically acceptable acid-addition salt thereof, hereinfter referred to as an active ingredient.

The pharmaceutical compositions may be made by methods well known in the art, using conventional pharmaceutically acceptable diluents or carriers.

A particular ointment formulation is prepared by dispersing an active ingredient as defined above in a suitable organic diluent, for example soft paraffin, optionally in the presence of an amulsifying and/or thickening agent, for example sorbitan monostearate.

A particular gel formulation is prepared by adding a gelling agent, for example carboxy-polymethylene, to a solution of an active ingredient as defined above in a suitable organic solvent, for example isopropyl alcohol.

A particular emulsion formulation, for example a cream or a lotion, is prepared by mixing an active ingredient as defined above with a suitable conventional emulsifying system and water.

A pharmaceutical composition according to this aspect of the invention may contain in addition to an active ingredient as defined above, at least one known pharmaceutical agent selected from: corticosteroids, for example fluocinolone acetonide, prednisolone, flumethasone pivalate, betamethasone valerate, hydrocortisone or dexamethasone; phosphodiesterase inhibitors, for example theorphylline or caffeine; antibacterial agents, for example oxytetracycline, gentamicin, neomycin, gramicidin, chlorhexidine or cetyltrimethylammonium bromide; anti-fungal agents, for example griseofulvin or nystatin; antihistamines, for example diphenhydramine or chlorphenamine; local anaesthetics, for example amylocaine, benzocaine or procaine; and emollients, for example calomine.

In addition the compositions of the invention may also contain conventional excipients such as colours, chelating agents, dispersing agents or preservatives as desired.

The invention is illustrated but not limited by the following Examples in which:

(i) unless otherwise stated, all procedures were carried out at room temperature (in the range 18°–26° C.) and at atmospheric pressure;

(ii) all evaporations were performed by rotary evaporation under reduced pressure;

(iii) nuclear magnetic resonance (NMR) data, where given, is present in the form of chemical shifts ($\delta$ values) for characteristic protons, relative to tetramethyl silane (TMS) as standard, determined in $d_6$DMSO as solvent (unless stated otherwise) and at 100 MHz;

(iv) the compounds of formula I in general had satisfactory microanalyses but in cases of doubt characteristic NMR spectral data is given;

(v) melting points given are those actually obtained and are intended to serve as a guide when repeating the Examples and are not necessarily the absolute values for fully crystalline compounds; and (vi) yields, where given, are purely illustrative and are not to be construed as the maximum attainable.

EXAMPLES 1–3

A solution of 3',4'-bis(pivaloyloxy)phenyl-glyoxal (0.9 g.) and $N^1$-(2-amino-2-methylpropyl)-$N^2$-benzoylglycinamide (0.67 g.), in acetic acid (2 ml.) and acetonitrile (10 ml.) was stirred for 30 minutes and treated with sodium cyanoborohydride (0.34 g.). The reaction mixture was stirred overnight and then evaporated under high vacuum. The residue was dissolved in ethyl acetate (50 ml.) and the solution washed with 10% v/v aqueous acetic acid (20 ml.). The aqueous layer was extracted with ethyl acetate (2×50 ml.) and the combined organic layers were washed with saturated sodium chloride solution, dried (MgSO$_4$) and evaporated. The residue was dissolved in ether and then filtered. The filtrate was treated with a slight excess of a freshly prepared ethereal solution of hydrogen bromide. The solid which deposited was separated and crystallised from ethanol/ether to give 1-3,4-bis(pivaloyloxy)phenyl]-2-{2-[(N-benzoylglycyl)amino]-1,1-dimethyl-ethylamino}ethanol hydrobromide (Example 1), as a solid (0.3 g.), m.p. 127°–129° C.

In a similar manner, but starting from the appropriate glycinamide derivative, there were obtained 1-[3,4-bis(-pivaloyloxy)phenyl]-2-{2-[(N-phenylacetylglycyl)amino]-1,1-dimethyl-ethylamino}ethanol hydrobromide (Example 2) in 35% yield, m.p. 145°–150° C., (microanalysis, found: C, 57.9; H, 6.7; N, 6.1; $C_{32}H_{45}N_3O_7$·HBr requires: C, 57.8; H, 6.9; N, 6.3%); and 1-[3,4-bis(pivaloyloxy)phenyl]-2-{2-[(N-phenoxyacetylglycyl)amino]-1,1-dimethyl-ethylamino}ethanol hydrobromide (Example 3) in 22% yield, m.p. 124°–126° C., (microanalysis, found: C, 53.7; H, 7.1; N, 6.1; $C_{32}H_{43}N_3O_8$·HBr requires: C, 53.6; H, 6.8; N, 5.9%)

The glycinamide starting materials were obtained as follows:

A mixture of phenylacetylglycine (10.0 g.), N-methyl morpholine (5.78 ml.) and chloroform (60 ml.) was stirred for 5 minutes. After cooling to −23° C., ethyl chloroformate (4.7 ml.) was added rapidly to the mixture during 1 minute, whereupon the temperture of the mixture rose to −15° C. After stirring for 1 minute, 1,2-diamino-2-methyl-propane (5.4 ml.) was added rapidly to the reaction mixture and the temperature was allowed to rise to room-temperature. After 1 hour at room temperature, the reaction mixture was poured into water (50 ml.) and the organic layer discarded. The aqueous layer was basified with excess potassium carbonate, and extracted with chloroform (4×100 ml.). The combined extracts were dried (MgSO$_4$) and evaporated. Trituration and filtration of the solid residue with ether gave $N^1$-(2-amino-2-methylpropyl)-$N^2$-phenylacetylglycinamide as a solid (8.8 g.), m.p. 150°–155° C.

In a similar manner using hippuric acid (N-benzoylglycine) and N-(phenoxy-acetyl)glycine, there were obtained $N^1$-(2-amino-2-methylpropyl)-$N^2$-benzoylglycinamide as a solid, m.p. 104°–105° C.; and $N^1$-(2-amino-2-methylpropyl)-$N^2$-(phenoxy-acetyl)glycinamide as a solid, m.p. 80°–4° C., respectively.

3',4'-Bis(pivaloyloxy)phenylglyoxal was obtained as follows:

A suspension of 3',4'-dihydroxy-acetophenone (13.1 g., 0.08 mole) in chloroform (320 ml.) was cooled in an ice bath to 0°–5° C. A solution of pivaloyl chloride (19.2 ml., 0.16 mole) in chloroform (80 ml.) and a solution of triethylamine (22.2 ml., 0.16 mole) in chloroform (80 ml.) were added dropwise simultaneously to the stirred suspension during 10 minutes. The reaction mixture was stirred at 0°–5° C. for a further 1 hour and then was poured into a mixture of 2N-hydrochloric acid (100 ml.) and ice (200 g.). The mixture was extracted with chloroform (3×150 ml.), and the extracts washed successively with water (100 ml.), 10% w/v sodium carbonate solution (100 ml.), water (100 ml.) and brine (100 ml.). After drying (MgSO$_4$) the combined extracts were evaporated to give crude 3',4'-bis(pivaloyloxy)acetophenone as an oil (23.1 g.) which was used without purification.

A solution of bromine (3.15 ml., 0.061 mole) in chloroform (50 ml.) was added dropwise at room temperature to a stirred solution of 3',4'-bis(pivaloyloxy)acetophenone (19.5 g., 0.061 mole) and t-butyl acetate (8.2 ml., 0.06 mole) in chloroform (150 ml.) containing a catalytic amount of anhydrous aluminium chloride (0.2 g.). The reaction mixture was stirred at room temperature for 1 hour after the addition was complete, chromatographic silica gel (75 g.) was then added and the mixture evaporated in vacuo. The residual solid was added to the top of a column of dry chromatographic silica-gel (1 kg., previously deactivated by addition of 10% w/w water and then equilibrated with 10% v/w of a 5% v/v solution of ethyl acetate in toluene). The column was developed by elution with a 5% v/v solution (1.1 l.) of ethyl acetate in toluene. The column was then eluted with ethyl acetate (2×500 ml.) and the fractions collected were monitored by thin layer chromatography (TLC) (on silica plates developed in a 50% v/v mixture of ethyl acetate and toluene). The later fractions were combined and evaporated to give 2-bromo-3'-4'-bis(pivaloyloxy)-acetophenone as an oil (14.2 g.) which rapidly crystallised to give a solid of m.p. 64°–66° C.

A solution of 2-bromo-3'-4'-bis(pivaloyloxy)acetophenone (2 g.) in dimethyl sulphoxide (10 ml.) was allowed to stand for 18 hours at room-temperature, then poured into ice-water and extracted with ether (3×60 ml.).

The ether solution was washed with water (50 ml.) and brine (50 ml.), dried (MgSO$_4$) and evaporated to give 3',4'-bis(pivaloyloxy)phenylglyoxal as an oil (1.8 g.); infra-red $\nu$max.: 1760 cm$^{-1}$ (ester<C=O), 1690 cm$^{-1}$ (—CO.CHO); δ(CDCl$_3$): 8.2–7.1 (complex, aromatic —H), 1–35 (18 H, singlet —C.C$\underline{H}_3$).

EXAMPLE 4

A solution of 3,4-bis(pivaloyloxy)phenylglyoxal (0.9 g.) and N$^1$-(2-amino-2-methylpropyl)-N$^2$-[N-(phenylacetyl)glycyl]glycinamide (0.86 g.) in acetic acid (2 ml.) and acetonitrile (10 ml.) was stirred for 30 minutes and then treated with sodium cyanoborohydride (0.34 g.). The reaction mixture was stirred overnight and then evaporated under high vacuum. The residue was dissolved in ethyl acetate (60 ml.) and the solution was washed successively with 10% v/v acetic acid solution (20 ml.), saturated sodium bicarbonate solution (20 ml.) and then saturated sodium chloride solution (20 ml.), dried and evaporated. The residue was dissolved in ether, and treated with ethereal hydrogen bromide as described in Example 1. The crude salt (0.6 g.) which deposited was dissolved in the least quantity of methanol and purified by preparative layer chromatography on silica gel plates using methanol-chloroform 1:4 v/v as eluant. The silica containing the major component was removed and extracted with methanol. The extracts were filtered and then evaporated. The residue was dissolved in ether and the solution treated with ethereal hydrogen bromide. The salt which formed was crystallised from ethanol/ether to give 1-[3,4-bis(pivaloyloxy)phenyl]-2-{2-[(N-benzoylglycyl)glycylamino]1,1-dimethyl-ethylamino}ethanol hydrobromide (Example 4), as a solid (0.1 g.), m.p. 110°–115° C. (microanalysis, found: C, 55.8; H, 7.3; N, 7.6; C$_{34}$H$_{48}$N$_4$O$_8$.HBr. ½ H$_2$O requires: C, 55.8; H, 6.8; N, 7.6%).

The starting material N$^1$-(2-amino-2-methylpropyl)-N$^2$-[N-(phenylacetyl)glycyl]glycinamide was obtained as a solid in 65% yield, m.p. 209°–210° C. (after crystallisation from ethanol) using a similar procedure to that described for the starting materials in Examples 1–3, but from [N-(phenylacetyl)glycyl]glycine and 1,2-diamino-2-methylpropane.

The preparation of [N-(phenylacetyl)glycyl]-glycine is described in Fench Patent Specification No. 1,010,560 (*Chemical Abstracts* Vol. 51, 13908 g.)

EXAMPLES 5–30

The following groups of compounds of formula I (A$^1$=methylene; R$^2$ and R$^3$=methyl) were obtained as their hydrobromide salts (unless otherwise stated) in yields in the range 20–70% starting with the appropriate glyoxal of formula III and amino compound of formula IV (A$^1$=methylene; R$^2$ and R$^3$=methyl) using a modified procedure to that described in Example 1. The modifications relate to the purification of the compound of formula I as its free base, and involve chromatographing the crude free base (obtained by evaporation of the ethyl acetate extracts) on chromatographic silica gel (particle size 0.04–0.063 mm) (80–100 parts by weight per part of free base) using chloroform containing 1–5% by volume of methanol as eluant. The purified free base thus obtained is then dissolved in the minimum volume of chloroform and acidified with ethereal hydrogen bromide (or hydrogen chloride as appropriate) and the mixture evaporated to give the compound of formula I as its hydrobromide (or hydrogen chloride) salt.

| Group I (Examples 5–14) : R$^1$ = 3,4-bis(pivaloyloxy)phenyl: | | | |
|---|---|---|---|
| Example | [CO . Y . NH]$_n$ | Q | Physical Characteristics |
| 5 | COCH$_2$CH$_2$NH (β-alanyl) | CO . Ph | foam (Note a) |
| 6 | βalanyl | CO . CH$_2$Ph | m.p. 122–127° C. C$_{33}$H$_{47}$N$_3$O$_7$ . HBr requires: C, 58.4; H, 6.9; N, 6.1% found: C, 58.1; H, 7.1; N, 5.8% |
| 7 | CO . CHCH$_3$ . NH (L-alanyl) | CO . Ph | m.p. 110–112° C. C$_{32}$H$_{45}$N$_3$O$_7$ . HBr . 2H$_2$O requires: C, 53.5; H, 7.2; N, 5.8% found: C, 53.2; H, 6.5; N, 5.7 |
| 8 | L-alanyl | CO . CH$_2$Ph | m.p. 111–113° C. C$_{33}$H$_{47}$N$_3$O$_7$ . HBr . 6H$_2$O requires: C, 50.4; H, 7.6; N, 5.3% found: C, 50.1; H, 7.5; N, 5.7% |
| 9 | L-alanyl | CO . CH$_2$OPh | m.p. 95–98° C. C$_{33}$H$_{47}$N$_3$O$_8$ . HBr . 3H$_2$O requires: C, 52.9; H, 7.2; N, 5.6% found: C, 52.3; H, 7.2; N, 5.6% |
| 10 | D-alanyl | CO . Ph | m.p. 158–162° C. C$_{32}$H$_{45}$N$_3$O$_7$ . HBr . H$_2$O requires: C, 54.7; H, 7.1; N, 6.4% found: C, 55.1; H, 7.0; N, 6.3% |
| 11 | CO . CH(CH$_2$Ph)NH (L-phenylalanyl) | CO . Ph | m.p. 145–150° C. (Note b) C$_{38}$H$_{49}$N$_3$O$_7$ . HBr requires: N, 5.7%; found: N, 5.4% |
| 12 | [COCH$_2$NH]$_2$ (glycyl . glycyl) | CO . CH$_2$OPh | m.p. 155–158° C. (Note c) |
| 13 | COCH$_2$NH . CO . CHCH$_3$ . NH (glycyl . L-alanyl) | CO . Ph | m.p. 145–155° C. C$_{34}$H$_{48}$N$_4$O$_8$ . HBr requires: C, 56.6; H, 6.8; N, 7.7% found: C, 52.0; H, 6.7; |

-continued

| Group I (Examples 5-14) : $R^1$ = 3,4-bis(pivaloyloxy)phenyl: | | | |
|---|---|---|---|
| Example | $[CO.Y.NH]_n$ | Q | Physical Characteristics |
| 14 | CO . CHCH$_3$ . NH . COCH$_2$NH (L-alanyl . glycyl) | CO . Ph | N, 7.7%<br>m.p. 152–158° C.<br>$C_{34}H_{48}N_4O_8$ . 1.5HBr . 4H$_2$O<br>requires: C, 48.7; H, 6.8;<br>N, 6.6; Br, 14.3%; found:<br>C, 48.2; H, 6.5; N, 6.4;<br>Br, 14.1% |

Note a:
NMR (δ) : 8.8–8.2 (2-NHCO + $\overset{+}{N}H_2$); 8.0–7.2 (8H, complex, aromatic, H); 8.85 (2H, complex, benzoyl ortho-aromatic H); 5.0 (CH . OH + H$_2$O); 3.8–2.8 (6H, complex, CH$_2$NH); 2.5 (2H, complex, CH$_2$CO); 1.28 [24H, singlet, C(CH$_3$)$_2$ + 2 C(CH$_3$)$_3$].
Note b:
NMR (δ) : 8.80 [1H, CH(CH$_2$Ph) . NHCO]; 8.4 (1H, triplet, CH$_2$NHCO); 7.8 (2H, 2 doublets, benzoyl ortho-aromatic H); 7.6–7.0 (11H, complex, aromatic H), 6.5 (1H, broad singlet, OH); 5.03 + 4.8 [2H, complex, CHOH + CH(CH$_2$Ph)NH]; 3.6–2.8 (complex, CH$_2$Ph + CH$_2$N); 1.3 [24H, singlet, C(CH$_3$)$_2$ + 2 C(CH$_3$)$_3$].
Note c:
NMR (δ) : 8.9–8.0 (4H, NHCO + $\overset{+}{N}H_2$); 7.5–6.8 (8H, complex, aromatic H); ~ 5.0 (complex, CHOH + H$_2$O); 4.6 (2H, singlet CH$_2$OPh); 3.9 (4H, complex, NHCH$_2$CO); 3.6–2.8 (4H, broad, CH$_2$NH); 1.3 [24H, singlet, C(CH$_3$)$_2$ + 2C(CH$_3$)$_3$].

| Group II (Examples 15-17): $R^1$ = 3,5-bis(pivaloyloxy)-phenyl | | | |
|---|---|---|---|
| Example | $[CO.Y.NH]_n$ | Q | Physical Characteristics |
| 15 | glycyl | CO . Ph | glass, m.p. 190–195° C.<br>(Note a) |
| 16 | L-alanyl | CO . CH$_2$OPh | m.p. 105–106° C.<br>$C_{33}H_{45}N_3O_8$ . HBr . 2.5H$_2$O requires:<br>C, 53.6; H, 7.2; N, 5.7% found:<br>C, 53.4; H, 7.2; N, 6.0% |
| 17 | L-phenylalanyl | CO . Ph | m.p. 110–111° C.<br>$C_{38}H_{49}N_3O_7$ . HBr . 2H$_2$O requires:<br>C, 58.8; H, 6.9; N, 5.4%;<br>found: C, 58:8; H, 6.9; N, 5.6% |

Note a:
NMR (δ): 8.76 (1H, triplet, NHCO); 8.50 (2H, broad singlet, $\overset{+}{N}H$); 8.21 (1H, triplet, NHCO); 7.9 (2H, complex, benzoyl ortho-H); 7.6–7.3 (3H, complex, benzoyl meta- and para-H); 7.1 [2H, doublet, bis(-pivaloyloxy)phenyl-H2, and -H6]; 6.9 [1H, triplet, bis(pivaloyloxy)-phenyl-H4]; 5.0 (1H, doublet, CHOH); 3.95 (2H, doublet, NHCH$_2$CO); 3.7–3.0 (complex, CH$_2$N); 1.29 [24H, singlet, C(CH$_3$)$_2$ + 2 C(CH$_3$)$_3$].

Group III (Examples 18-24) : $R^1$ is a radical of the formula:-

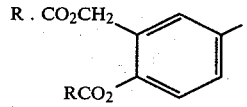

| Example | R | $[COYNH]_n$ | Q | Physical Characteristics |
|---|---|---|---|---|
| 18 | t-butyl | glycyl | CO . CH$_2$Ph | m.p. 75–79° C. (free base)<br>(Note a) |
| 19 | t-butyl | β-alanyl | CO . CH$_2$Ph | m.p. 76–80° C. (hydrochloride)<br>$C_{34}H_{49}N_3O_7$ . HCl . 1.5H$_2$O<br>requires: C, 60.5; H, 7.9;<br>N, 6.2%; found: C, 60.7;<br>H, 7.8; N, 6.0% |
| 20 | n-butyl | glycyl | CO . Ph | m.p. 101–104° C.<br>$C_{32}H_{45}N_3O_7$ . HBr . 2H$_2$O<br>requires: C, 54.3; H, 7.1;<br>N, 6.0%; found: C, 54.5;<br>H, 7.0; N, 6.0% |
| 21 | n-butyl | L-alanyl | CO . CH$_2$Ph | m.p. 68–78° C.<br>$C_{34}H_{49}N_3O_7$ . HBr . H$_2$O<br>requires: C, 57.5; H, 7.3;<br>N, 5.9% found: C, 57.1;<br>H, 7.4; N, 6.7% |
| 22 | n-butyl | β-alanyl | CO . CH$_2$OPh | foam (Note b) |
| 23 | isopropyl | L-alanyl | CO . Ph | m.p. 72–82° C.<br>$C_{31}H_{43}N_3O_7$ . HBr requires:<br>C, 57.2; H, 6.8%; found:<br>C, 57.4; H, 7.1% (Note c) |
| 24 | isopropyl | glycyl | CO . CH$_2$Ph | foam (Note d) |

-continued

Group III (Examples 18-24): $R^1$ is a radical of the formula:-

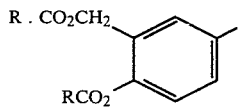

| Example | R | [COYNH]$_n$ | Q | Physical Characteristics |
|---|---|---|---|---|
| | | glycyl | | |

Note a:
NMR (δ) : 7.7 (1H, complex, NHCO); 7.6–6.8 (8H, complex, aromatic H); ~5.0[broad singlet, CHOH + (CH$_3$)$_3$CCO$_2$CH$_2$ + H$_2$O]; 3.9 [2H, doublet (J 7 c/s), NHCH$_2$CO]; 3.55 (2H, singlet, COCH$_2$Ph); 3.2–2.7 (4H, complex CH$_2$N); 1.38 [9H, singlet, (CH$_3$)$_3$CO$_2$ . C]; 1.16 [15H, singlet, (CH$_3$)$_3$CO$_2$CH$_2$ + C(CH$_3$)$_2$].

Note b:
NMR (δ) : 8.8–8.0 (4H, complex, 2NHCO + $\overset{+}{\text{NH}}_2$); 7.8–6.8 (8H, complex, aromatic H); 5.05 + 4.97 [3H, singlet + doublet, CHOH + CH$_3$(CH$_2$)$_3$ . CO$_2$CH$_2$]; 3.7–2.8 (6H, complex, CH$_2$N; 2.4 [6H, multiplet, CH$_2$CO (+ DMSO)]; 1.6–1.0 + 1.28 [14H : complex, CH$_2$ + singlet, C(CH$_3$)$_2$]; 0.9 (6H, multiplet, CH$_3$(CH$_2$)$_3$CO].

Note c:
NMR (δ) : [3H, doublet (J 7 c/s), NHCO]; 8.05 [1H, triplet (J 3 c/s), NHCO]; 7.9 (2H, multiplet, benzoyl ortho-H); 7.5–6.8 (6H, complex, aromatic H); 5.9 (1H, broad singlet, CHOH); 4.95 + 4.85 [3H, singlet + broad singlet, (CH$_3$)$_2$CHCO$_2$ CH$_2$ + CHOH]; 4.42 (1H, multiplet, CHCH$_3$); 3.6–2.5 [6H, complex, CH$_2$N + (CH$_3$)$_2$ CH CO(+ H$_2$O]; 1.28 + 1.1 [21H, doublet (J7c/s), CHCH$_3$; + quartet, C(CH$_3$)$_2$ + (CH$_3$)$_2$ + (CH$_3$)$_2$CH]

Note d:
NMR : 8.8–8.0 (5H, complex, 3NHCO + $\overset{+}{\text{NH}}_2$); 7.7–6.7 (8H, complex, aromatic H); 6.1 (1H, broad, CHOH); 4.98 + 4.95 [3H: singlet, (CH$_2$)$_2$CHCO$_2$CH$_2$; broad singlet, CHOH]; 4.5 (2H, singlet, CH$_2$ O Ph); 3.8 (4H, multiplet, NHCH$_2$CO); 3.6–2.5 [complex, CH$_2$N + (CH$_3$)$_2$ CHCO (+H$_2$O]; 1.1 [18H, quartet, (CH$_3$)$_2$CH + C(CH$_3$)$_2$].

Group IV (Examples 25-30):

| Example | $R^1$ | [CO . Y . NH]$_n$ | Q | Physical Characteristics |
|---|---|---|---|---|
| 25 | Phenyl | glycyl | COCH$_2$Ph | m.p. 130–140° C. C$_{22}$H$_{29}$N$_3$O$_3$ . 2HBr. 0.5H$_2$O requires: C, 47.7; H, 5.8; N, 7.6% found: C, 47.8; H, 6.0; N, 8.1% |
| 26 | 2-Chlorophenyl | glycyl | COCH$_2$Ph | m.p. 72–75° C. (free base) (note a) |
| 27 | 3,5-Dichloro-4-aminophenyl | glycyl | COCH$_2$OPh | foam (note b) (free base) |
| 28 | 3,5-Dichloro-4-aminophenyl | L-alanyl | CO . CH$_2$OPh | m.p. 120–125° C. C$_{23}$H$_{30}$N$_4$O$_4$Cl$_2$ . 2HBr. 3H$_2$O requires: C, 38.7; H, 5.0; N, 7.8%; found: C, 36.3; H, 4.7; N, 7.4; Br, 27.6 (note c) |
| 29 | 3,5-Dichloro-4-aminophenyl | β-alanyl | CO . CH$_2$OPh | m.p. 165–169° C. (free base) C$_{23}$H$_{30}$N$_4$O$_4$Cl$_2$ . 0.25 H$_2$O requires: C, 54.5; H, 6.1; N, 11.1%; found: C, 54.2; H, 6.0; N, 10.8% |
| 30 | 3,5-Dichloro-4-aminophenyl | glycyl . glycyl | OC . CH$_2$Ph | m.p. 105–108° C. (free base) (note d) |

Note a:
NMR (CDCl$_3$, δ): 8.8–8.5 (complex, NHCO + NH); 7.4–6.8 (9H, complex, aromatic H); 5.2 (1H, doublet, CHOH); 3.9 (2H, doublet, NHCH$_2$CO); 3.6 (2H, singlet, COCH$_2$Ph); 3.36 [2H, doublet, C(CH$_3$)$_2$CH$_2$NH]; 3.1 + 2.7 (2H, doublet + multiplet, CHOH . CH$_2$NH), 1.2 [6H, doublet, C(CH$_3$)$_2$].

Note b:
NMR (δ): 8.25 (1H, complex, NHCO); (1H, complex, NHCO); 7.4–6.8 (7H, complex, aromatic H); 5.4 (2H, singlet, aromatic NH$_2$); 4.53 (3H, singlet, COCH$_2$OPh + CHOH); 3.83 (2H, doublet, NHCH$_2$CO); 3.2 [2H, complex, C(CH$_3$)$_2$CH$_2$NH]; 3.0–2.7 (2H, multiplet, CHOH . CH$_2$NH); 1.1 [6H, singlet, C(CH$_3$)$_2$].

Note c:
NMR (δ): 9.0 –9.1 (complex, 2NHCO + NH$_2$); 7.5–6.8 (7H, complex, aromatic H); 4.86 (1H, multiplet, CHOH); 4.7–4.3 [3H, complex, COCH$_2$OPh + CH(CH$_3$)]; 3.4[2H, complex, C(CH$_3$)$_2$CH$_2$NH]; 3.3–2.8 (2H, complex, CHOH . CH$_2$NH); 1.32 + 1.28 [9H, doublet (J6 c/s), CH(CH$_3$);singlet C(CH$_3$)$_2$].

Note d:
NMR (δ); 8.35 (1H, triplet, NHCO); 8.15 (1H, triplet, NHCO); 7.81 (1H, triplet, NHCO); 7.28 (7H, singlet, aromatic H); 5.42 (2H, singlet, aromatic NH$_2$); 4.55 (1H, multiplet, CHOH); 3.77 (4H, doublet, NHCH$_2$CO); 3.6–2.6 [complex, CHOH . CH$_2$NH (+ H$_2$O); 3.50 (singlet, COCH$_2$Ph); 1.12 [6H, singlet, C(CH$_3$)$_2$].

The following amino compounds of formula IV ($A^1$=methylene; $R^2$ and $R^3$=methyl) required as starting materials were obtained from the corresponding acids of formula VII and 1,2-diamino-2-methylpropane using similar procedures to those described for the analogous starting materials in Examples 1-3:

| No. | [CO . Y . NH]$_n$ | Q | m.p. (°C.) |
|---|---|---|---|
| 1 | CO . CH$_2$CH$_2$NH (β-alanyl) | CO . Ph | 92–94 |
| 2 | β-alanyl | CO . CH$_2$Ph | 100–102 |
| 3 | β-alanyl | CO . CH$_2$OPh | 73–75 |
| 4 | CO . CHCH$_3$ . NH (L-alanyl) | CO . Ph | 105–107 |
| 5 | L-alanyl | CO . CH$_2$Ph | 144–146 |
| 6 | L-alanyl | CO . CH$_2$OPh | oil (Note a) |
| 7 | D-alanyl | CO . Ph | 72–75 (hydrate) |
| 8 | CO . CH(CH$_2$Ph)NH (L-phenylalanyl) | CO . Ph | 146–148 |
| 9 | CO . CH$_2$NH . CO . CH$_2$NH (glycyl . glycyl) | CO . CH$_2$OPh | 175–180 |
| 10 | CO . CH$_2$NH . CO . CHCH$_3$ . NH (glycyl . L-alanyl) | CO . Ph | foam (Note b) |
| 11 | CO . CHCH$_3$ . NH . CO . CH$_2$NH (L-alanyl . glycyl) | CO . Ph | oil (Note c) |

Note a:
NMR (δ): 8.9–8.5 (2H, complex, NHCO); 8.5–7.7 (5H, complex, aromatic H); 4.65 + 4.48 (3H: multiplet, CHCH$_3$; singlet COCH$_2$OPh); 3.5 + 3.22 [4H: singlet, NH$_2$; doublet (J 7 c/s), NH$_2$C(CH$_3$)$_2$CH$_2$NH]; 1.43 (3H, doublet, CHCH$_3$); 1.13 (6H, singlet, C(CH$_3$)$_2$).

Note b:
NMR (δ): 8.1–7.1 (8H, complex, aromatic H + NHCO); 4.67 (1H, triplet, CHCH$_3$); 3.90 (2H, complex, NHCH$_2$CO); 3.10 [2H, doublet (J 4 c/s) H$_2$NC(CH$_3$)$_2$CH$_2$NH]; 2.22 (2H, singlet, NH$_2$); 1.50 [3H, doublet (J 5 c/s), CHCH$_3$]; 1.10 [6H, singlet, C(CH$_3$)$_2$].

Note c:
NMR (δ): 8.2–7.2 (8H, complex, NHCO + aromatic H); 4.57 [1H, triplet (J 8 c/s), CHCH$_3$]; 4.18 (2H, complex, NHCH$_2$CO); 3.16 [2H, doublet, H$_2$NC(CH$_3$)$_2$CH$_2$NH]; 2.5 (complex, NH$_2$); 1.38 [3H, doublet (J 8 c/s), CHCH$_3$]; 1.07 [6H, singlet, C(CH$_3$)$_2$].

The starting acids of formula VII may be obtained by acylation procedures well known in the art. A typical procedure is illustrated for N-benzoyl-L-alanine below:

L-alanine (17.8 g., 0.2 mole) was dissolved in 2N-sodium hydroxide solution (120 ml.) with cooling to 0°–5° C. Benzoyl chloride (30.0 g., 0.22 mole), followed by 2N-sodium hydroxide (120 ml.), were then added to the solution in ten equal and alternate portions with vigorous intermittent shaking and ice cooling. The mixture was continually maintained at an alkaline pH. After completion of the addition, the mixture was shaken for 15 minutes at room-temperature. The clear solution obtained was acidified with concentrated hydrochloric acid to pH2 whilst ice cooling to give N-benzoyl L-alanine as a solid (27.8 g.), m.p. 137°–139° C.

Using a similar procedure, the following acids of formula VII were obtained:

The necessary glyoxal starting materials of formula III were obtained by conventional dimethylsulphoxide oxidation of the corresponding 2-bromoacetophenone derivatives. This procedure is illustrated by the following preparation of 3′,5′-bis(pivaloyloxy)phenylglyoxal:

A solution of 2-bromo-3′,5′-bis(pivaloyloxy)acetophenone (8.6 g.) in dimethylsulphoxide (35 ml.) was left at room temperature for 2 days and then poured into an excess of ice-water. The mixture was extracted with ethyl acetate (3×100 ml.). The extracts were washed successively with saturated sodium bicarbonate solution (50 ml.), water (3×50 ml.) and saturated sodium chloride solution (50 ml.), and then evaporated to yield 3′,5′-bis(pivaloyloxy)phenylglyoxal as an oil (7.0 g.), ν max. 1760 cm$^{-1}$ (ester carbonyl) and 1690 cm$^{-1}$ (CO.CHO).

The majority of the glyoxal starting materials were prepared in a similar manner and had similar properties, and all were used without further purification.

| No. | [CO . Y . NH]$_n$ | Q | Physical Characteristics |
|---|---|---|---|
| 1 | CO . CHCH$_3$ . NH (L-alanyl) | CO . CH$_2$Ph | m.p. 52–55° C. |
| 2 | L-alanyl | CO . CH$_2$OPh | m.p. 192–193° C. |
| 3 | CO . CH(CH$_2$Ph) . NH (L-phenylalanyl) | CO . Ph | m.p. 136–138° C° |
| 4 | D-alanyl | CO . Ph | m.p. 120–125° C. (softens at ~ 100° C.) |
| 5 | CO . CH$_2$NH . CO . (CH$_3$) . NH (glycyl . L-alanyl) | CO . Ph | m.p. 165–167° C. |
| 6 | CO . CH(CH$_3$) . NH . CO . CH$_2$NH (L-alanyl . glycyl) | CO . Ph | m.p. 188–190° C. |
| 7 | glycyl . glycyl | CO . CH$_2$OPh | m.p. 192–193° C. |
| 8 | COCH$_2$CH$_2$NH (β-alanyl) | CO . Ph | m.p. 115–118° C. |
| 9 | β-alanyl | COCH$_2$Ph | m.p. 106–107° C. |
| 10 | β-alanyl | COCH$_2$OPh | m.p. 118–122° C. |

Note:
In the above Examples when the radical [CO . Y . NH] is other than a glycyl (CO . CH$_2$NH) or β-alanyl (CO . CH$_2$CH$_2$NH) radical, in all cases amino acids having the indicated D- or L-configuration were used as original starting materials. However it will be appreciated that some racemisation may have occured during the reaction sequence leading to the compounds of formula I (especially of those compounds wherein Q is a benzoyl radical) and that the final products may not necessarily be completely optically pure insofar as the radical [CO . Y . NH] is concerned.

4'-Amino-3',5'-dichlorophenylglyoxal was obtained as a solid hydrate, m.p. 95°–98° C., in 58% by oxidation of 4'-amino-3',5'-dichlorophenylacetophenone (12.0 g.) with selenium dioxide (10.0 g.) in a mixture of dioxan (60 ml.) and water (2 ml.), at 95° C. for four hours, followed by evaporation of the filtered mixture.

The corresponding 2-bromoacetophenone derivatives were obtained in known manner by bromination of the acetophenone as illustrated below for 3'-valeryloxymethyl-4'-valeryloxy-2-bromoacetophenone:

A solution of bromine (4.2 g.) in chloroform (20 ml.) was added dropwise to a cooled stirred solution of 3'-valeryloxy-methyl-4'-valeryloxyacetophenone (8.5 g.) in chloroform (100 ml.). During the addition, the temperature was maintained at 0°–5° C. by the addition of small pieces of solid carbon dioxide. The solution was then washed with 10% w/v sodium carbonate solution (3 × 100 ml.) water (2 × 100 ml.) and saturated brine (100 ml.). The organic phase was dried ($MgSO_4$), filtered, and evaporated yielding 3'-valeryloxymethyl-4'-valeryloxy-2-bromoacetophenone (6 g., 57%), which was judged to be sufficiently pure by IR and TLC [$SiO_2$: 50 v/v EtOAc/petrol (60°–80°)] for use without further purification or characterisation.

The acetophenone was obtained as follows:

Sodium hydride (2.0 g.) was added in portions to stirred valeric acid (150 ml.) over a period of 15 minutes. 3'-Acetoxymethyl-4'-acetoxy-acetophenone (40 g.) was then added, and the mixture was heated to 160° C. and maintained at this temperature with stirring for 15 hours. The mixture was then concentrated by distilling under reduced pressure while maintaining the temperature at 160° C. The gummy residue was cooled and dissolved in ether (500 ml.). This solution was washed with 10% w/v sodium carbonate solution (3 × 250 ml.), water (2 × 500 ml.) and saturated brine (250 ml.). The organic phase was dried ($MgSO_4$), filtered and evaporated to give a brown oil. This was distilled under high vacuum to give 3'-valeryloxymethyl-4'-valeryloxy-acetophone as a colourless viscous liquid (16.0 g. 30%): NMR $\delta$ ($CDCl_3$): 7.9–7.0 (3H, 1,2,4 aromatic substitution pattern); 5.0 (2H, sharp singlet, $CO_2\underline{CH_2}$); 2.5 (3H, sharp singlet, $COCH_3$); 2.55–2.15 (4H, complex, $CH_3(CH_2)_2\underline{CH_2}CO_2$ and $CH_3(CH_2)_2\underline{CH_2}CO_2CH_2$); 1.8–1.2 (8H, complex, $CH_3\underline{CH_2CH_2}CH_2CO_2O$); 1.1–0.8 (6H, overlapping triplets, $CH_3(CH_2)_3CO_2$).

3'-Isobutyryloxymethyl-4'-isobutyryloxy-2-bromoacetophenone was obtained in an analogous manner as an oil having a satisfactory IR spectrum and pure by TLC [$SiO_2$: 50% v/v EtOAc/petrol (b.p. 60°–80° C.)]. The intermediate 3'-isobutyryoxymethyl-4'-isobutyryloxyacetophenone was also isolated as a liquid: NMR ($\delta$) ($CDCL_3$): 8.2–7.1 (3H, 1,2,4-aromatic H pattern); 5.1 (2H, singlet $CO_2CH_2$); 2.55+2.67 (5H; singlet, $COCH_3$+doublet, $CHCO_2$); 1.21+1.15 [12H, 2 doublets (J 8.3 c/s), $(CH_3)_2CH$].

EXAMPLE 31

Using a procedure similar to that described in Example 4 there was obtained 1-[3,4-bis(pivaloyloxy)phenyl]-2-{2-[(N-phenylacetyl-glycyl)amino]ethylamino}-ethanol hydrobromide as a solid (0.25 g.), m.p. 146°–148° C. (microanalysis: $C_{30}H_{41}N_3O_7HBr.H_2O$ requires: C, 55.0; H, 6.7; N, 6.4%; found: C, 54.6; H, 6.5; N, 6.4%), starting with 3,4-bis(pivaloyloxy)phenyl-glyoxal (0.9 g.) and $N^1$-(2-aminoethyl)-$N^2$-(phenylacetyl)glycinamide (0.635 g.). The latter starting material was obtained as follows:

A mixture of N-(phenylacetyl)glycine methyl ester (35.0 g.) and ethylene diamine (34 ml.) was heated at 95°–100° C. for 2 days. Excess ethylene diamine was then evaporated and the residue was dissolved in water, any insoluble material being removed by filtration. The aqueous filtrate was evaporated to dryness using coevaporation with toluene to remove last traces of water. The residue obtained was washed with ether to give $N^1$-(2-aminoethyl)-$N^2$-(phenylacetyl)glycinamide (37.0 g.), m.p. 132°–137° C. (after crystallisation from ethanol/ether).

EXAMPLE 32

A mixture of powdered 1-[3,4-bis(pivaloyloxy)-phenyl]-2-{2-[(N-benzoyl-glycyl)amino]-1,1-dimethylethylamino}ethanol hydrobromide (0.1 w/w), sorbitan monostearate (2 w/w), liquid paraffin (7 w/w) and cetostearyl alcohol (9 w/w) was fused together at 60°–70° C. Water (79.9 w/w) was then added with rapid stirring and the mixture was slowly cooled to room temperature to give a homogeneous cream suitable for therapeutic use.

Using a similar procedure there may be obtained a cream containing as active ingredient a compound of formula I described in any one of Examples 2–31.

EXAMPLE 33

A solution of 1-[3,4-bis(pivaloyloxy)phenyl]-2-{2-[(N-benozyl-glycyl)amino]-1,1-dimethyl-ethylamino}ethanol hydrobromide (0.1 w/w) in 2-propanol (30 w/w) was mixed with water (66.9 w/w) with rapid stirring and further addition of a carboxymethylene gelling agent ("Carbopol" *940, available from B. F. Goodison Chemical Co., Cleveland, Ohio, U.S.A.) (3 w/w) until a highly dispersed gel, suitable for therapeutic use was obtained.

[*"Carbopol" is a trade-mark].

Using a similar procedure, a gel containing as active ingredient a compound of formula I as described in any one of Examples 2–31 may be obtained.

EXAMPLE 34

A mixture of powdered 1-[3,4-bis(pivalyloxy)-phenyl]-2-{2-[(N-phenylacetyl-glycyl)amino]-1,1-dimethylethylamino}ethanol hydrobromide (0.5 w/w) in liquid paraffin (10 w/w) was added to molten white soft paraffin (89.5 w/w). The resultant mixture was cooled to room temperature with fast stirring until a uniformly dispersed ointment was obtained, suitable for therapeutic use.

In a similar manner an ointment containing as active ingredient a compound of formula I as described in Example 1 or in any one of Examples 3–31 may be obtained.

What is claimed is:

1. A 1-phenyl-2-aminoethanol derivative of the formula:

$R^1.CH(OH).CH_2.NH.CR^2R^3.A^1.NH.[CO.Y.NH]_n.Q$ wherein $R^1$ is a 3,4-bis[(2-12C) alkanoyloxy]phenyl, 3,5-bis[2-12C)-alkanoyloxy]phenyl, 3-[(2-12 C)alkanoyloxymethyl]-4-[(2-12 C)alkanoyloxy]phenyl or 3,5-dichloro-4-aminophenyl radical; $R^2$ and $R^3$ are independently hydrogen or (1-4 C)alkyl radicals; $A^1$ is a (1-4 C)alkylene diradical; Y is a (1-4 C)alkylene diradical optionally bearing a (1-4 C)alkyl or benzyl substituent; n is an integer from 1 to 4; and Q is a benzoyl, phenylacetyl or phenoxyacetyl radical optionally bearing a nuclear substituent selected from halogeno, (1–4 C)alkyl, (1–4 C)alkoxy and trifluoromethyl radicals; provided that when n is other than 1, Y is the individual diradicals of the formula [CO.Y.NH] may have the same or different values; or a pharmaceutically acceptable acid-addition salt thereof.

2. A compound as claimed in claim 1 wherein the (2–12 C)-alkanoyloxy radical of $W^1$ is a 2,2-dimethylpropionyloxy, isobutyryloxy, n-pentanoyloxy or 3,3-dimethylbutyryloxy radical; $R^2$ and $R^3$ are independently hydrogen or methyl radicals; $A^1$ is a methylene or ethylene diradical; Y is a methylene, ethylene or trimethylene diradical optionally bearing a methyl, ethyl or benzyl substituent; and Q is a benzoyl, phenylacetyl or phenoxyacetyl radical optionally bearing a nuclear substituent selected from fluoro, chloro, bromo, methyl, methoxy and trifluoromethyl radicals.

3. A compound as claimed in claim 1 wherein the diradical of the formula [CO.Y.NH] is a glycyl, alanyl, β-alanyl or phenylalanyl diradical.

4. A compound as claimed in claim 1, wherein the diradical of the formula [CO.Y.NH]$_n$ is a glycyl, alanyl, β-alanyl, phenylalanyl, glycylglycyl, glycylalanyl or alanylglycyl diradical.

5. A compound as claimed in claim 1, wherein $R^2$ and $R^3$ are both hydrogen or methyl radicals; $A^1$ is a methylene diradical; the diradical of the formula [CO.Y.NH]$_n$ is a glycyl, alanyl, phenylalanyl or glycylglycyl diradical; and Q is a benzoyl, phenylacetyl or phenoxyacetyl radical.

6. A 1-phenyl-2-aminoethanol derivative selected from the group consisting of 1-[3,4-bis(pivaloyloxy)-phenyl]-2-{2-[(N-benzoyl-glycyl)amino]-1,1-dimethylethylamino}ethanol, 1-[3,4-bis(pivaloyloxy)phenyl]-2-{2-[(N-phenylacetyl-glycyl)amino]-1,1-dimethylethylamino}ethanol, 1-[3,4-bis(pivaloyloxy)phenyl-2-{2-[(N-phenylacetylglycyl)glycyl-amino]-1,1-dimethylethylamino}ethanol, 1-(3,5-dichloro-4-aminophenyl)-2-{2-[(N-phenoxyacetyl-glycyl)amino]-1,1-dimethylethylamino}-ethanol, 1-(3,5-dichloro-4-aminophenyl)-2-{2-[(N-phenylacetyl-glycyl)glycyl-amino]-1,1-dimethyl-ethylamino}-ethanol, and the pharmaceutically acceptable acid-addition salts thereof.

7. A pharmaceutically acceptable acid-addition salt as claimed in claim 1 which is a salt derived from hydrochloric, hydrobromic, phosphoric, sulphuric, oxalic, tartaric, lactic, fumaric, citric, acetic, slaicylic, benzoic, β-naphthoic, methane sulphonic or adipic acid.

8. A method of treatment of an area of inflammation affecting the skin of a warm blooded animal which comprises topically administering to said area an effective amount of a compound of formula I, or a pharmaceutically acceptable acid-addition salt thereof:

$R^1.CH(OH).CH_2.NH.CR^2R^3.A^1.NH.[CO.Y.NH]_nQ$   I wherein $R^1$ is a radical of the formula:

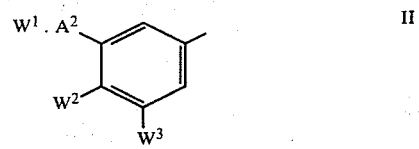

in which $W^1$ is a (2–12 C)alkanoyloxy, $A^2$ is a direct bond or a methylene diradical, one of $W^2$ and $W^3$ is hydrogen, and the other of $W^2$ and $W^3$ is a (2–12 C)alkanoyloxy radical; or $R^1$ is a phenyl, 2-chlorophenyl or 3,5-dichloro-4-aminophenyl radical; $R^2$ and $R^3$ are independently hydrogen or (1–4 C)alkyl radicals; $A^1$ is a (1–4 C)alkylene diradical; Y is a (1–4 C)alkylene diradical optionally bearing a (1–4 C)alkyl or benzyl substituent; n is an integer from 1 to 4; and Q is a benzoyl, phenylacetyl or phenoxyacetyl radical optionally bearing a nuclear substituent selected from halogeno, (1–4 C)alkyl, (1–4 C)alkoxy and trifluoromethyl radicals; provided that when n is other than 1, Y is the individual diradicals of the formula [CO.Y.NH] may have the same or different values.

9. A pharmaceutical composition which comprises a compound of formula I or a pharmaceutically acceptable salt thereof as claimed in claim 1, in association with a pharmaceutically acceptable diluent or solvent, and in a form suitable for topical administration.

* * * * *